United States Patent
Ishii et al.

(10) Patent No.: US 9,353,348 B2
(45) Date of Patent: May 31, 2016

(54) METHOD FOR PRESERVING ENZYME

(71) Applicant: MITSUBISHI RAYON CO., LTD., Chiyoda-ku (JP)

(72) Inventors: Emi Ishii, Yokohama (JP); Masahito Oda, Yokohama (JP)

(73) Assignee: MITSUBISHI RAYON CO., LTD., Chiyoda-ku (JP)

( * ) Notice: Subject to any disclaimer, the term of this patent is extended or adjusted under 35 U.S.C. 154(b) by 0 days.

(21) Appl. No.: 14/381,363

(22) PCT Filed: Feb. 19, 2013

(86) PCT No.: PCT/JP2013/053955
§ 371 (c)(1),
(2) Date: Aug. 27, 2014

(87) PCT Pub. No.: WO2013/129179
PCT Pub. Date: Sep. 6, 2013

(65) Prior Publication Data
US 2015/0050718 A1 Feb. 19, 2015

(30) Foreign Application Priority Data

Feb. 28, 2012 (JP) ................................. 2012-041610
Oct. 30, 2012 (JP) ................................. 2012-239614

(51) Int. Cl.
*C12N 1/06* (2006.01)
*C12N 1/20* (2006.01)
*C12N 9/88* (2006.01)
*C12N 9/96* (2006.01)

(52) U.S. Cl.
CPC *C12N 1/20* (2013.01); *C12N 1/066* (2013.01); *C12N 9/88* (2013.01); *C12N 9/96* (2013.01); *C12Y 402/01084* (2013.01)

(58) Field of Classification Search
CPC ............ C12N 1/066; C12N 1/20; C12N 9/88; C12N 9/96; C12N 15/78; C12N 9/1051; C12N 9/1077; C12N 11/02; C12N 11/08; C12N 9/001; C12N 9/1029; C12N 9/80; C12Y 402/01084; C12Q 1/25; G01N 33/58; G01N 33/6803; G01N 33/6842; G01N 33/6848; Y10S 530/812; Y10T 436/182; Y10T 436/24; Y10T 436/25; Y10T 436/25125; Y02P 20/52; C12P 13/02; C12P 21/00; C12P 21/02; C12P 7/40
See application file for complete search history.

(56) References Cited

U.S. PATENT DOCUMENTS

| | | | |
|---|---|---|---|
| 5,705,382 A | 1/1998 | Endo et al. |
| 5,707,382 A | 1/1998 | Sierocuk et al. |
| 5,807,730 A | 9/1998 | Ito et al. |
| 5,910,432 A | 6/1999 | Ito et al. |

FOREIGN PATENT DOCUMENTS

| | | |
|---|---|---|
| JP | 9 275978 | 10/1997 |
| JP | 3163224 | 5/2001 |
| JP | 2003 144144 | 5/2003 |
| JP | 2003 219870 | 8/2003 |
| JP | 2008 154552 | 7/2008 |
| WO | 2006 062189 | 6/2006 |
| WO | 2011 007725 | 1/2011 |

OTHER PUBLICATIONS

International Search Report Issued May 7, 2013 in PCT/JP13/053955 Filed Feb. 19, 2013.
Extended European Search Report issued Dec. 3, 2014 in Patent Application No. 13755463.0.
Takakazu Endo, et al., "Nitrile hydratase of *Rhodococcus* sp. N-774 Purification and amino acid sequences" FEBS Letters, vol. 243, No. 1, XP025600499, Jan. 1989, pp. 61-64.
Isco Endo, et al., "An enzyme controlled by light: the molecular mechanism of photoreactivity in nitrile hydratase" Trends in Biotechnology, vol. 17, No. 6, XP004167257, Jun. 1999, pp. 244-248.
Teruyuki Nagamune, et al., "Purification of Inactivated Photoresponsive Nitrile Hydratase" Biochemical and Biophysical Research Communications, vol. 168, No. 2, XP026787072, Apr. 1990, pp. 437-442.
Karina Kubiak, et al., "Molecular Dynamics Simulations of the Photoactive Protein Nitrile Hydratase" Biophysical Journal, vol. 94, No. 10, XP002732498, May 2008, pp. 3824-3838.

*Primary Examiner* — Debbie K Ware
(74) *Attorney, Agent, or Firm* — Oblon, McClelland, Maier & Neustadt, L.L.P.

(57) ABSTRACT

The problem is to provide a method for inexpensively and simply preserving an enzyme of a microbial biomass obtained by culturing and improve the enzyme activity during preservation. Provided is a method for preserving nitrile hydratase, characterized in that microbes having nitrile hydratase activity are cultured while being protected from light, and the resulting biomass is crushed using a high-pressure homogenizer and preserved while being protected from light.

13 Claims, No Drawings

METHOD FOR PRESERVING ENZYME

TECHNICAL FIELD

The present invention relates to a method for preserving an enzyme of microorganisms having nitrile hydratase activity, a method for activating it, and a method for producing activated nitrile hydratase.

BACKGROUND ART

An enzyme produced by microorganisms is used in many areas as a catalyst for chemical conversion reaction. In particular, by using nitrile hydratase, nitrilase, or the like which has an ability of hydrating or hydrolyzing a nitrile group, it is possible to produce at low cost the amides, carboxylic acids, α-hydroxycarboxylic acids or the like that are important in chemical industry. Further, by using this enzyme having an optically specific hydrating ability or an optically specific hydrolyzing ability, it is also possible to produce optically active carboxylic acids, amino acids, α-hydroxycarboxylic acids or the like that are important as a raw material for producing pharmaceuticals and agrochemicals.

For a chemical conversion reaction which uses an enzyme derived from microorganisms as a catalyst, it is necessary to preserve stably the cultured and collected micro organisms until their use. Specifically, preservation should be made such that the catalytic activity of the enzyme is not lost or lowered due to decomposition or lysis as caused by contamination. Accordingly, inactivation, decomposition, or lysis of a microbial enzyme is inhibited during the preservation of microbial cells by preserving generally in the presence of a stabilizing agent, a metabolic inhibitor, or high-concentration salts, and the enzyme is then used for a chemical conversion reaction. For a case of not adding a stabilizing agent or the like, preservation by freezing, cooling, or stirring under aeration to maintain the activity of an enzyme is known.

In case of microorganisms having nitrile hydratase activity, a method for preservation in an aqueous solution which contains inorganic salts at a high concentration (Patent Document 1), a method for preservation by freezing (Patent Document 2), a method for performing stirring under aeration with a controlled pH (Patent Document 3), or the like are known.

Meanwhile, for the purpose of enhancing convenience of a microbial catalyst user, a method for isolating solid matters after disrupting microbial cells and purifying the microbial enzyme is known (Patent Document 4).

CITATION LIST

Patent Document

Patent Document 1: Japanese Patent No. 3163224
Patent Document 2: JP 2003-219870 A
Patent Document 3: JP 2003-144144 A
Patent Document 4: WO 2011/007725 A

DISCLOSURE OF THE INVENTION

However, having complicated steps, the aforementioned preservation method of a related art is not economically favorable. Further, from the viewpoint of having lower enzyme activity, it is yet to be recognized as a satisfactory method. For example, the method of using an aqueous solution containing inorganic salts at a high concentration, which is described in Patent Document 1, requires performing washing during a following step, and thus it may exhibit an influence on product quality and also the production steps become complicated. Further, the method for preservation by freezing, which is described in Patent Document 2, has a problem that the operation involved with freezing and melting is cumbersome and also the enzyme activity is either lost or lowered accompanying the operation. The method for preservation by stirring under aeration with a controlled pH, which is described in Patent Document 3, requires acid and alkali chemicals or facilities and power for performing the stirring under aeration. In Patent Document 4, a method for disrupting microbial cells and performing centrifugal separation after acid and heat treatment is described. However, from the viewpoint of having lower enzyme activity according to the progress of reaction steps, there is a need for improvement.

An object of the invention is to provide a method for preserving an enzyme of microbial cells, which have been obtained by culture, at low cost and with convenience compared to a method of a related art.

The inventors of the invention conducted intensive studies to solve the aforementioned problems. It was consequently found that, by disrupting the microbial cells after culture of the microorganisms having nitrile hydratase activity under protection against light using a high-pressure type homogenizer and preserving them while protecting them from light, an enzyme of microbial cells can be preserved inexpensively and simply and also the enzyme activity is enhanced during the preservation. Specifically, according to finding of a method for preserving an enzyme of microbial cells which satisfies the aforementioned problem, the present invention is completed.

Specifically, the present invention relates to a method for inexpensively and simply preserving an enzyme of microbial cells obtained by culture and enhancing the enzyme activity during preservation compared to a method of a related art. The subject matter is a method for preserving an enzyme having nitrile hydratase activity, which is characterized in that microbes having nitrile hydratase activity are cultured while being protected from light, and the resulting microbial cells are disrupted using a high-pressure type homogenizer and preserved while being protected from light.

A method more preferred as the method of the present invention relates to the following aspect, that is, suspension of disrupted microbial cells is preserved by a certain method; and certain microorganisms having nitrile hydratase activity is used.

As an another preferred aspect, the followings can be mentioned: the suspension of disrupted microbial cells is preserved at 4 to 37° C.; the suspension of disrupted microbial cells is preserved for 4 to 24 hours; and the microorganisms belonging to the genus *Rhodococcus* or the genus *Pseudonocardia* are used.

The subject matter of the present invention is also a method of activating an enzyme having nitrile hydratase activity; and a method for producing activated nitrile hydratase, which is characterized in that microbial cells obtained by culturing microorganisms having nitrile hydratase activity while protecting them from light are disrupted using a high-pressure type homogenizer, and preserved while being protected from light.

According to the present invention, by disrupting microbial cells which are obtained by culture while being protected from light and suspended in a dispersion medium using a high-pressure type homogenizer, and preserving them while being protected from light, a state in which the activity of an enzyme such as nitrile hydratase is maintained, that is, preserved, with no decomposition or deterioration of the enzyme even without performing aeration or stirring, or having pH control or heating treatment, can be achieved. Further, according to the present invention, the enzyme activity can be improved during preservation. In other words, labor or cost that is believed to be required for a preservation method of a related art can be significantly reduced so that an industrially satisfactory method for preserving a microbial enzyme is provided.

MODE FOR CARRYING OUT THE INVENTION

Hereinbelow, the present invention is explained in detail. However, the following embodiments are an example to explain the present invention and it is not intended to limit the present invention to the embodiments. As long as it remains within the subject matter of the present invention, the present invention can be implemented in many forms.

In the present invention, the microorganisms having nitrile hydratase activity have a property of producing a desired enzyme catalyst and accumulating it within a microbial cell or secreting it to the outside of the microbial cell. Examples of the microorganisms include microorganisms that are isolated from nature and genetic recombinant microorganisms. Representative examples of the microorganisms include microorganisms belonging to the genus *Rhodococcus*, the genus *Gordona*, the genus *Pseudomonas*, the genus *Pseudonocardia*, and the genus *Geobacillus* which have nitrile hydratase activity. Further, genetic recombinant microorganisms introduced with the nitrile hydratase gene of those microorganisms can be also mentioned. Among them, the genus *Rhodococcus*, the genus *Pseudonocardia*, and the recombinant *E. coli* and the recombinant genus *Rhodococcus* to which the nitrile hydratase gene of those microorganisms have been introduced are industrially preferable. Specific examples of the microorganisms of the genus *Rhodococcus* include *Rhodococcus rhodochrous* J-1 strain described in JP 6-55148 B and *Rhodococcus rhodochrous* NCIMB41164 described in WO 2005/054456 A. *Rhodococcus rhodochrous* J-1 strain has been deposited on Sep. 18, 1987 with the Patent Organism Depository Center of National Institute of Industrial Science and Technology, an Independent Administrative Institution (zip code: 305-8566, Central 6, 1-1-1 Higashi, Tsukuba, Ibaraki, Japan (ditto in the present specification)) under accession number FERM BP-1478. Further, NCIMB41164 strain has been deposited on Mar. 5, 2003 with National Collection of Industrial and Marine Bacteria (NCIMB) (NCIMB Ltd Ferguson Building Craibstone Estate Bucksburn Aberdeen AB21 9YA) under accession number NCIMB41164. Specific examples of the genus *Pseudonocardia* include *Pseudonocardia thermophila* JCM3095 which has been described in JP 09-275978 A. This strain has been deposited with the same Patent Organism Depository Center under accession number FERM BP-5785.

In the present invention, one type selected from the above microorganisms can be used alone or two or more of them can be used in combination.

Culture of the microorganisms having nitrile hydratase activity can be performed according to common conditions that are suitable for culturing microorganisms except that culture is performed under protection against light.

The nitrile hydratase indicates an enzyme having ability of hydrolyzing a nitrile compound and producing a corresponding amide compound. The nucleic acids encoding the nitrile hydratase and examples of the sequence are as those described in Patent Document 2. The nucleic acids can be expressed in a cell of microorganisms after being introduced thereto by a common molecular biological method (with regard to the molecular biological methods, see the followings: Sambrook, Fritsch and Maniatis, "Molecular Cloning: A Laboratory Manual" 2nd Edition (1989), Cold Spring Harbor Laboratory Press). Specifically, in the present invention, an enzyme obtained from natural microorganisms having nitrile hydratase activity can be used or an enzyme obtained by expressing the nucleic acids encoding the nitrile hydratase in microbial cells can be used. In the present invention, one type selected from the above enzymes can be used alone or two or more of them can be used in combination.

In the present invention, the term "preserve" means preservation of disrupted microbial cells in a tank or a container. At that time, it is possible to perform stirring or aeration so as not to have uneven concentration in the tank or container. However, in the present invention, keeping without performing stirring or aeration is also possible. In the present invention, the term "keeping" means that the disrupted microbial cells are preserved in a tank or a container without having stirring or aeration. With regard to a method of protection against light in the present invention, it is possible to preserve the disrupted microbial cells in a tank protected from light or a sealed container in a dark room.

In the present invention, the preservation temperature varies depending on the microorganisms which produce an enzyme, the type of an enzyme, or the like. However, by having the enzyme activity as an indicator, it is possible to set suitable preservation temperature.

In the present invention, the preservation can be generally performed at room temperature. However, from the viewpoint of activating an enzyme, it is preferably performed at 4 to 37° C., more preferably at 4 to 25° C., and even more preferably at 4 to 15° C. When the preservation temperature is lower than 4° C., not only a suspension of microbial cells may freeze but also the cost related to cooling may increase. On the other hand, when it is higher than 37° C., the nitrile hydratase activity may be lowered depending on a microbial enzyme.

In the present invention, the preservation period varies depending on the micro organisms which produce an enzyme, the type of an enzyme, the preservation temperature or the like. However, by having the enzyme activity as an indicator, it is possible to set a suitable preservation period. The preservation period can be generally 4 to 24 hours. However, it is more preferably 6 to 24 hours. When the preservation period is shorter than 4 hours, the nitrile hydratase activity may not be sufficiently enhanced. On the other hand, when it is longer than 24 hours, the nitrile hydratase activity may be lowered due to decomposition of suspension of microbial cells, depending on the temperature or microbial enzyme.

When a microbial enzyme is preserved according to the method of the present invention, the enzyme activity is activated compared to a case in which protection against light is not performed. With regard to the nitrile hydratase activity, the nitrile hydratase activity after preservation is generally more than 100% compared to the nitrile hydratase activity before the preservation. It is maintained preferably at 103% or higher, more preferably at 110% or higher, or even more preferably at 120%.

The nitrile hydratase activity can be measured by any method known in the pertinent technological field. For example, the measurement can be made by comparing the reaction rate of producing acrylamide relative to the substrate (for example, acrylonitrile) before starting the preservation and after the preservation.

In the present invention, the term "dispersion medium" means a solution used for suspending microbial cells as a subject for disruption. Any type of a dispersion medium can be used, and it can be a liquid medium used for microbial cell culture or a medium obtained by replacing the liquid medium used for culture with an aqueous solution of organic acid.

The component of the aqueous solution of organic acid is not particularly limited if it does not inhibit the enzyme activity. Examples thereof include carboxylic acids such as acrylic acid, formic acid, acetic acid, propionic acid, butyric acid, or oxalic acid. Among them, from the viewpoint of maintaining the quality of acrylamide, acrylic acid is preferable.

Preparation of a suspension of disrupted cells of the present invention is preferably performed for the microbial cells obtained by culture, before performing a chemical treatment (for example, glutaraldehyde treatment disclosed in JP 7-265091 A). For the method for disruption, a high-pressure type homogenizer that can disrupt the microbial cells while they are suspended in a dispersion medium can be used. Examples of the high-pressure type homogenizer include a French press and a continuous pressure type. The continuous pressure type allowing industrial obtainment of a suspension of disrupted cells in a large amount and also with stability is preferable. With regard to the disruption method, it is preferable to perform disruption using a high-pressure type homogenizer in a suspended state with a dispersion medium. The temperature at the time of disruption is, in order to avoid thermal degradation, preferably 0° C. to 37° C., and more preferably 0° C. to 25° C. The pressure at the time of disruption is not particularly limited if it is pressure allowing disruption of microbial cells. However, it is rather adjusted to 50 to 150 MPa, or preferably 70 to 120 MPa. The cell concentration at the time of disruption is not particularly limited. However, in dry microbial cells equivalent, it can be within the range of 0.1 to 30% by mass.

Meanwhile, in the present invention, it is also possible to preserve the suspension of disrupted cells and then a solid matter is isolated therefrom and used. The method for isolating a solid matter is not limited, but examples include centrifugal separation. The temperature at the time of isolating operation is preferably 0 to 37° C., and more preferably 0 to 25° C.

EXAMPLES

Hereinbelow, the method for carrying out the present invention is explained in greater detail in view of Examples. However, the Examples are given to illustrate the present invention and the present invention is not limited to them. In the following test examples (Examples, Comparative Examples, and Reference Examples), evaluation of the enzyme activity was performed by measuring the rate of hydration reaction when a supernatant obtained by centrifugal separation of cultured microbial cells after being preserved by a certain method is brought into contact with nitrile by a certain method described below.

Hereinbelow, the description "%" in Examples, Comparative Examples, and Reference Examples indicates % by mass.
<Production of Transformant of Genus Rhodococcus Having Nitrile Hydratase Gene>

As a transformant introduced with the nitrile hydratase gene derived from *Rhodococcus rhodochrous* J1, *Rhodococcus rhodochrous* ATCC12674/pSJ042 produced by the method described in JP 2008-154552 A was used.

With regard to the transformant introduced with the nitrile hydratase gene derived from *Pseudonocardia thermophila* JCM3095, the transformant *Rhodococcus rhodochrous* ATCC12674/pSJ-N02A, which has been obtained by introducing the plasmid pSJ-N02A described in JP 2011-200132 A to the ATCC12674 strain according to the same method as described therein, was used.

<Culture of Microbial Cells>
(1) Culture of Transformant of ATCC12674 Strain

To a 500 ml conical flask, 100 ml of the medium (pH 7.2) which has been prepared by dissolving the components of Table-1 in tap water was added and sterilized by autoclave at 121° C. for 20 minutes. To the medium, urea and kanamycin were added so as to have 0.1 g/L and 50 mg/L, respectively. After inoculating ATCC12674/pSJ042 or ATCC12674/pSJ-N02A, culture was performed for 72 hours at 30° C. and 230 rpm under protection against light. The medium components that are used in the test example are shown in Table-1.

(2) Culture of *Rhodococcus rhodochrous* J-1 Strain

To a 3 liter jar fermentor (manufactured by Takasugi Seisakusho), 2.5 liter of the medium (pH 7.0) which has been prepared by dissolving the components of Table-2 in tap water was added and sterilized by autoclave at 121° C. for 20 minutes. To the medium, 20 ml of *Rhodococcus rhodochrous* J-1 cultured in the same manner as above (1) were inoculated and cultured for 42 hours while being protected from light. The culture temperature was 35° C. The medium components that are used in the test example are shown in Table-2.

(3) Culture of *Rhodococcus rhodochrous* NCIMB-41164 Strain

To a 500 ml conical flask, 100 ml of the medium (pH 7.2) which has been prepared by dissolving the components of Table-3 in tap water was added and sterilized by autoclave at 121° C. for 20 minutes. To the resultant, urea was added so as to have 5.0 g/L. After inoculating *Rhodococcus rhodochrous* NCIMB-41164, culture was performed for 65 hours at 30° C. and 230 rpm under protection against light. The medium components that are used in the test example are shown in Table-3.

TABLE 1

| | |
|---|---|
| Glucose | 15 g/L |
| Yeast extract | 1 g/L |
| Na glutamate | 10 g/L |
| Potassium hydrogen phosphate | 0.5 g/L |
| Dipotassium hydrogen phosphate | 0.5 g/L |
| Magnesium sulfate heptahydrate | 0.5 g/L |
| Cobalt chloride hexahydrate | 0.01 g/L |

TABLE 2

| | |
|---|---|
| Fructose | 20 g/L |
| Polypeptone | 10 g/L |
| Na glutamate | 13 g/L |
| Potassium hydrogen phosphate | 2 g/L |
| Dipotassium hydrogen phosphate | 2 g/L |
| Magnesium sulfate heptahydrate | 1 g/L |
| Methyl urea | 0.32 g/L |
| Ethanol | 4 ml/L |
| Cobalt chloride hexahydrate | 0.1 g/L |

TABLE 3

| | |
|---|---|
| Glucose | 10 g/L |
| Yeast extract | 3 g/L |
| Peptone | 1 g/L |
| Potassium hydrogen phosphate | 0.3 g/L |
| Dipotassium hydrogen phosphate | 0.7 g/L |
| Magnesium sulfate heptahydrate | 0.5 g/L |
| Cobalt chloride hexahydrate | 0.01 g/L |

<Measurement of Concentration of Dry Microbial Cells>
"Concentration of dry microbial cells (dry microbial cell mass [%])" is represented by the ratio of dry mass of microbial cells that are contained in a suspension of microbial cells. Specifically, it is obtained by subtracting the ratio of the mass before and after drying the liquid layer that is obtained by drying for 3 hours with a dryer at 120° C. after separating the suspension of microbial cells into a microbial cell layer and a liquid layer substantially not containing microbial cells (percentage: salt concentration in supernatant [%]) from the ratio of the mass before and after drying the suspension of microbial cells in the same manner as above (percentage: ratio of dry residues from microbial solution [%]).
<Measurement of Nitrile Hydratase Activity>
The nitrile hydratase activity was calculated from the reaction rate for producing acrylamide by the supernatant from which solid matters have been removed after disrupting microbial cells. By adding an aqueous solution of acrylonitrile as a substrate to the supernatant, the reaction was initiated. After shaking for 10 minutes at 10° C., the reaction was terminated by filter separation of the microbial cells and addition of phosphoric acid. Analysis was then made by gas chromatography (GC-14B, manufactured by Shimadzu Corporation). As for the analysis conditions, a 1 meter glass column filled with Porapack PS (manufactured by Waters Company) was used, the column temperature was 210° C., and FID at 230° C. was used as a detector.

In the present invention, the enzyme activity of nitrile hydratase was measured as an amount of acrylamide (μmol) which is produced by 1 mg of microbial cells for one minute.

Test Example

Example 1

Dry microbial cell concentration was measured for ATCC12674/pSJ042 and ATCC12674/pSJ-N02A, which have been obtained by performing the culture as described above. Next, by a small-size microbe disrupting device PANDA2K (manufactured by Niro Soavi), which is a high-pressure type homogenizer, and using the suspension of microbial cells obtained by performing culture, the microbial cells were disrupted. The pressure for disruption was 100 MPa and the temperature at the time of disruption was 4° C. The suspension of disrupted microorganisms immediately after the preparation (Hour 0) and preserved for 4 to 24 hours by keeping it in a dark place at 4 to 37° C. was subjected to centrifugal separation for 5 minutes at 4° C. and 15000 rpm to obtain a supernatant. The nitrile hydratase activity of the supernatant was measured. Consequently, the relative values that are obtained when the activity at Hour 0 is 100 are shown in Table-4.

Reference Example 1

The effect of enhancing the enzyme activity was determined in the same manner as Example 1 except that the preservation temperature was changed to 50° C. Consequently, the relative values that are obtained when the activity at Hour 0 is 100 are shown in Table-4.

TABLE 4

|  | Microorganisms from which enzyme gene is derived | Dry microbial cell concentration [g/L] | Preservation temperature [° C.] | Preservation period [Hours] | Nitrile hydratase activity [-] |
|---|---|---|---|---|---|
| Example 1 | Rhodococcus rhodochrous J-1 | 6.1 | 4 | 4 | 112 |
|  |  |  |  | 24 | 110 |
|  |  |  | 15 | 4 | 110 |
|  |  |  |  | 24 | 103 |
|  | Pseudonocardia thermophila JCM3095 | 4.5 | 4 | 4 | 110 |
|  |  |  | 15 | 4 | 110 |
|  |  |  | 25 | 4 | 110 |
|  |  |  |  | 24 | 104 |
|  |  |  | 30 | 4 | 109 |
|  |  |  |  | 24 | 105 |
|  |  |  | 37 | 4 | 115 |
|  |  |  |  | 24 | 110 |
| Reference Example 1 | Rhodococcus rhodochrous J-1 | 6.1 | 50 | 4 | 3 |
|  |  |  |  | 24 | 0 |
|  | Pseudonocardia thermophila JCM3095 | 4.5 | 50 | 24 | 41 |

It was found that, by culturing microorganisms while protecting them from light and preserving the enzyme from the microbial cells for a period and at a temperature according to the enzyme while protecting them from light, the enzyme activity was enhanced. When the enzyme derived from the microorganisms that have been used in above Examples and Comparative Examples was used, the enzyme lost the activity at the preservation temperature of 50° C. so that no enzyme activating effect was obtained.

Example 2

The effect of enhancing the enzyme activity was determined in the same manner as Example 1 except that the microorganisms subjected to culture were *Rhodococcus rhodochrous* J1 and a 3 liter jar fermentor (manufactured by Takasugi Seisakusho) was used for the culture instead of a 500 ml conical flask. Meanwhile, the dry microbial cell concentration was 39.8 g/L after the culture. Consequently, the relative values that are obtained when the activity at Hour 0 is 100 are shown in Table-5.

Reference Example 2

The effect of enhancing the enzyme activity was determined in the same manner as Example 2 except that the preservation temperature was changed to 50° C. Consequently, the relative values that are obtained when the activity at Hour 0 is 100 are shown in Table-5.

Reference Example 3

The effect of enhancing the enzyme activity was determined in the same manner as Example 2 except that the preservation time was changed to 48 hours. Consequently, the relative values that are obtained when the activity at Hour 0 is 100 are shown in Table-5.

Comparative Example 4

The effect of enhancing the enzyme activity was determined in the same manner as Example 2 except that an ultrasonic wave generator (VP-300 manufactured by TAITEC) was used as a device for disruption. For the operation of ultrasonic disruption, 1 ml of the suspension of cultured microbial cells was collected in a 15 ml conical tube (manufactured by Corning) and the application was made for 5 minutes at an intensity of 20% under ice cooling. Consequently, the relative values that are obtained when the activity at Hour 0 is 100 are shown in Table-5.

Comparative Example 5

The effect of enhancing the enzyme activity was determined in the same manner as Example 2 except that the operation for protection against light was not performed. Consequently, the relative values that are obtained when the activity at Hour 0 is 100 are shown in Table-5.

cultured microbial cells are *Rhodococcus rhodochrous* NCIMB41164 and a manually operating French press (Model 5502, manufactured by Otake Seisakusho), which is high-pressure type homogenizer, was used for disrupting the microbial cells. Meanwhile, the dry microbial cell concentration was 5.4 g/L after the culture. Consequently, the relative values that are obtained when the activity at Hour 0 is 100 are shown in Table-6.

Reference Example 6

The effect of enhancing the enzyme activity was determined in the same manner as Example 3 except that the preservation temperature was changed to 50° C. Consequently, the relative values that are obtained when the activity at Hour 0 is 100 are shown in Table-6.

Reference Example 7

The effect of enhancing the enzyme activity was determined in the same manner as Example 3 except that the preservation period was changed to 48 hours. Consequently, the relative values that are obtained when the activity at Hour 0 is 100 are shown in Table-6.

Comparative Example 8

The effect of enhancing the enzyme activity was determined in the same manner as Example 3 except that an ultra-

TABLE 5

| | Homogenizer | Preservation temperature [° C.] | Preservation period [Hours] | Protection against light [Yes · No] | Nitrile hydratase activity [-] |
|---|---|---|---|---|---|
| Example 2 | High-pressure type | 4 | 6 | Yes | 111 |
| | | | 24 | Yes | 122 |
| | | 15 | 6 | Yes | 111 |
| | | | 24 | Yes | 129 |
| | | 25 | 6 | Yes | 117 |
| | | | 24 | Yes | 129 |
| | | 30 | 6 | Yes | 122 |
| | | | 24 | Yes | 121 |
| | | 37 | 6 | Yes | 123 |
| Reference Example 2 | | 50 | 24 | Yes | 91 |
| Reference Example 3 | | 30 | 48 | Yes | 96 |
| | | 37 | 48 | Yes | 95 |
| Comparative Example 4 | Ultrasonic wave type | 4 | 24 | Yes | 92 |
| Comparative Example 5 | High-pressure type | 25 | 24 | No | 95 |

It was found that, by culturing microbes while protecting them from light and keeping an enzyme from the microbial cells for a period and at a temperature according to the enzyme while protecting them from light, the enzyme activity was enhanced. When the enzyme derived from the microbes that have been used in above Examples, Comparative Examples, and Reference Examples was used, the enzyme activating effect was not obtained at the preservation temperature of 50° C. No enzyme activating effect was obtained either at the preservation temperature of 30 to 37° C. or preservation period of 48 hours. Meanwhile, by using a high-pressure type homogenizer, the enzyme activating effect was obtained.

Example 3

The effect of enhancing the enzyme activity was determined in the same manner as Example 1 except that the sonic wave generator (VP-300 manufactured by TAITEC) was used as a device for disruption. For the operation of ultrasonic disruption, 1 ml of the suspension of cultured microbial cells was collected in a 15 ml conical tube (manufactured by Corning) and the application was made for 5 minutes at an intensity of 20% under ice cooling. Consequently, the relative values that are obtained when the activity at Hour 0 is 100 are shown in Table-6.

Comparative Example 9

The effect of enhancing the enzyme activity was determined in the same manner as Example 3 except that the operation for protection against light was not performed. Consequently, the relative values that are obtained when the activity at Hour 0 is 100 are shown in Table-6.

TABLE 6

|  | Homogenizer | Preservation temperature [° C.] | Preservation period [Hours] | Protection against light [Yes · No] | Nitrile hydratase activity [-] |
|---|---|---|---|---|---|
| Example 3 | High-pressure type | 4 | 24 | Yes | 110 |
|  |  | 25 | 24 | Yes | 104 |
|  |  | 30 | 24 | Yes | 102 |
| Reference Example 6 |  | 50 | 24 | Yes | 38 |
| Reference Example 7 |  | 25 | 48 | Yes | 84 |
| Comparative Example 8 | Ultrasonic wave type | 25 | 24 | Yes | 90 |
| Comparative Example 9 | High-pressure type | 25 | 24 | No | 98 |

It was found that the enzyme activity could be enhanced by culturing microbes while protecting them from light and keeping the enzyme from the microbial cells for a period and at a temperature according to the enzyme while protecting them from light. In the case of using the enzyme derived from the microorganisms that have been used in above Examples, Comparative Examples, and Reference Examples, no enzyme activating effect was obtained when the cell disruption was made by using a ultrasonic wave type homogenizer. Further, without having protection against light during the preservation, the enzyme activating effect was not obtained.

The invention claimed is:

1. A method for preserving nitrile hydratase, said method comprising:
   (1) culturing a microorganism having a nitrile hydratase activity while protecting them from light,
   (2) disrupting the cultured microbial cells from the microorganism using a high-pressure type homogenizer, and
   (3) preserving the disrupted microbial cells for 4 to 24 hours at 4 to 37° C. while protecting them from light.

2. The method according to claim 1, wherein the microorganism having a nitrile hydratase activity is a microorganism belonging to the genus *Rhodococcus* or the genus *Pseudonocardia*.

3. The method of claim 1, wherein the microorganism having a nitrile hydratase activity belongs to the genus *Rhodococcus, Pseudonocardia, Pseudomonas, Pseudonocardia*, or *Geobacillus*, or is a genetic recombinant microorganism with an introduced nitrile hydratase gene.

4. A method for activating nitrile hydratase, said method comprising:
   (1) culturing a microorganism having a nitrile hydratase activity while protecting them from light,
   (2) disrupting the cultured microbial cells from the microorganism using a high-pressure type homogenizer, and
   (3) preserving the disrupted microbial cells for 4 to 24 hours at 4 to 37° C. while protecting them from light.

5. The method according to claim 4, wherein the microorganism having a nitrile hydratase activity is a microorganism belonging to the genus *Rhodococcus* or the genus *Pseudonocardia*.

6. The method of claim 4, wherein the microorganism having a nitrile hydratase activity belongs to the genus *Rhodococcus, Pseudonocardia, Pseudomonas, Pseudonocardia*, or *Geobacillus*, or is a genetic recombinant microorganism with an introduced nitrile hydratase gene.

7. A method for producing activated nitrile hydratase, said method comprising:
   (1) culturing a microorganism having a nitrile hydratase activity while protecting them from light,
   (2) disrupting the cultured microbial cells from the microorganism using a high-pressure type homogenizer, and
   (3) preserving the disrupted microbial cells for 4 to 24 hours at 4 to 37° C. while protecting them from light.

8. The method according to claim 7, wherein the microorganism having a nitrile hydratase activity is a microorganism belonging to the genus *Rhodococcus* or the genus *Pseudonocardia*.

9. The method of claim 7, wherein the microorganism having a nitrile hydratase activity belong to the genus *Rhodococcus, Pseudonocardia, Pseudomonas, Pseudonocardia*, or *Geobacillus*, or is a genetic recombinant microorganism with an introduced nitrile hydratase gene.

10. A method for producing nitrile hydratase, said method comprising:
    (1) culturing a microorganism having a nitrile hydratase activity while protecting them from light,
    (2) disrupting the cultured microbial cells from the microorganism using a high-pressure type homogenizer, and
    (3) preserving the disrupted microbial cells while protecting them from light.

11. The method according to claim 10, wherein the microorganism having a nitrile hydratase activity is a microorganism belonging to the genus *Rhodococcus* or the genus *Pseudonocardia*.

12. The method according to claim 10, wherein the preservation of the disrupted microbial cells is performed at a temperature of from 4 to 37° C.

13. The method of claim 10, wherein the microorganism having a nitrile hydratase activity belong to the genus *Rhodococcus, Pseudonocardia, Pseudomonas, Pseudonocardia*, or *Geobacillus*, or is a genetic recombinant microorganism with an introduced nitrile hydratase gene.

\* \* \* \* \*